United States Patent [19]

Singhal

[11] Patent Number: 4,566,335

[45] Date of Patent: Jan. 28, 1986

[54] METHOD AND APPARATUS FOR TESTING FIBER REINFORCED PLASTIC LAMINATES

[75] Inventor: Surendra N. Singhal, Houston, Tex.

[73] Assignee: Shell Oil Company, Houston, Tex.

[21] Appl. No.: 641,154

[22] Filed: Aug. 16, 1984

[51] Int. Cl.$^4$ .............................................. G01N 3/20
[52] U.S. Cl. ...................................... 73/849; 73/161; 73/852; 73/856
[58] Field of Search .................. 73/849, 852, 856, 73, 73/161

[56] References Cited

U.S. PATENT DOCUMENTS

| 1,308,410 | 7/1919 | Girl .......................................... 73/161 |
| 2,527,208 | 10/1950 | Berry et al. .............................. 73/73 |
| 2,670,624 | 3/1954 | Faris et al. .............................. 73/852 |

FOREIGN PATENT DOCUMENTS 463678 12/1913 France .................................. 73/849

OTHER PUBLICATIONS

Steklov et al., "Method of Stress Corrosion Testing Uniaxial Bending and Constant Strain", Ind. Lab. (USA), vol. 36, No. 8, pp. 1244–1247, Aug. 1970.

*Primary Examiner*—Anthony V. Ciarlante

[57] ABSTRACT

An apparatus for applying and measuring a variable bending load to a fiber reinforced plastic test specimen under desired temperature and humidity conditions. The apparatus comprises a frame member including means for holding the ends of the test specimen while applying a bending load to the center of the test specimen.

3 Claims, 1 Drawing Figure

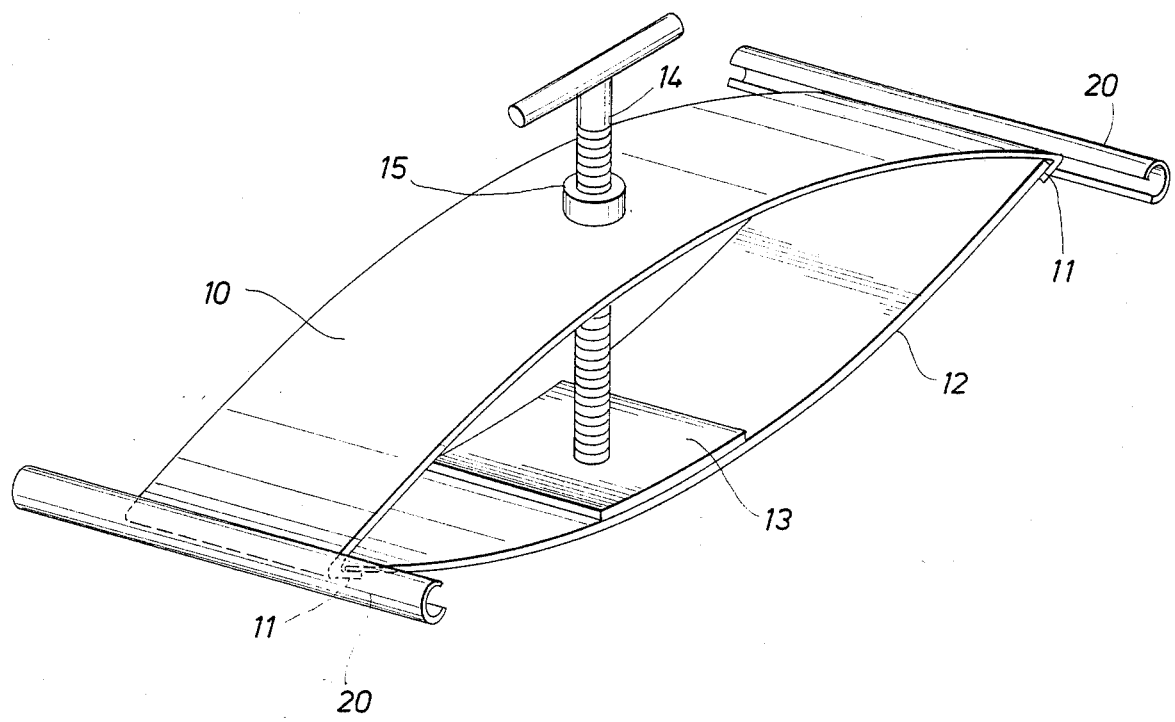

METHOD AND APPARATUS FOR TESTING FIBER REINFORCED PLASTIC LAMINATES

BACKGROUND OF THE INVENTION

The present invention relates to a test apparatus and particularly to an inexpensive apparatus for applying a bending load to a fiber reinforced plastic laminate. In the development of fiber reinforced plastic laminates for various uses, particularly automotive uses, it is desirable to accumulate data relating to the response of the laminates under various conditions. This is particularly important when laminates are used for spring components on automotive vehicles, particularly trucks and the like. It can be appreciated that laminates used in springs are subjected to bending loads under varying temperature and humidity conditions. Thus, it is important to know the response of various laminates under varying bending loads and atmospheric conditions.

Obviously, it is impossible to construct full size springs if a large number of various combinations of fibers and plastics are to be tested. The various combinations of fiber and plastic can be molded in small inexpensive test specimens. While it is possible to test the molded specimens in presently available test equipment, the equipment is rather large and cumbersome. The large size of the equipment does not lend itself to use in controlled atmospheric conditions or in the testing of a large number of specimens. Also, it is impossible to measure the weight gain of a specimen as a result of moisture adsorption because of the size of the equipment.

SUMMARY OF THE INVENTION

The present invention provides an apparatus for retaining a test specimen and applying a bending load to the specimen. In particular, the apparatus is a relatively light weight metal frame that permits testing of the specimen under any humidity and temperature conditions. The moisture absorption of the test specimen can usually be determined by merely weighing the combination of the apparatus and specimen before and after the tests since the frame is comparable in weight to the weight of the specimen. The frame has an arcuate shape with the ends bent towards the center to retain the specimen. Normally, the test specimen will consist of a relatively thin elongated strip of the laminate. The bending load is applied to the center of the test specimen by a combination of a screw member and a threaded opening in the top of the arcuate shaped portion of the frame.

The combination of the test specimen and apparatus can be placed in autoclaves or similar devices where the temperature and humidity may be controlled at desired levels. Normally, the test specimen will be subjected to relatively high temperatures, for example 175° F., under relatively high humidity, i.e., more than 90 percent humidity. Under these conditions most laminates absorb considerable moisture which results in their early deterioration. Obviously, materials that are to be used in automotive components must be capable of withstanding considerable moisture and temperature without failure. Under normal conditions the flexing of a spring will produce temperatures in the laminate that are considerably higher than atmospheric temperatures.

BRIEF DESCRIPTION OF THE DRAWINGS

The present invention will be more easily understood from the following description when taken in conjunction with the attached drawing in which:

The sole FIGURE shows a pictorial view of the apparatus with a test specimen of a laminate installed therein.

DESCRIPTION OF PREFERRED EMBODIMENTS

Referring to the drawing, there is shown an apparatus suitable for holding an elongated test specimen of fiber reinforced plastic laminate and applying a bending load thereto. The apparatus comprises an arcuate shaped frame member 10 which is preferably formed of steel or a similar metal. The ends 11 of the frame member are bent inwardly towards the center of the member to provide a lip for supporting the ends of the test specimen 12. The bending load is applied to the test specimen by means of a bearing plate 13 which rests on the test specimen and a screw member 14. The screw member 14 threads through a threaded opening 15 in the arcuate shaped member and the bending stress imposed on the test member is controlled by the position of the screw member. Suitable tubular members 20 are secured to the ends of the arcuate shaped member to prevent the apparatus from rolling over during a test procedure.

Normally, the test specimen 12 will be approximately one inch wide by five inches long, and the frame member should be sized accordingly. A number of test specimens are placed in suitable holders and the group is placed in a controlled atmosphere, for example, an autoclave or similar device. The chamber should have means for controlling not only its temperature but its humidity. It has been found that if the temperature is raised to approximately 175 degrees and the humidity is at least 95 percent, results will be obtained that permit one to eliminate or discard those laminates which are unsatisfactory. After suitable laminate candidates have been selected, further and more exhaustive tests can then be carried out. The amount of moisture absorbed by the test specimens is easily determined by weighing the test specimen and sample holder prior to the beginning of the test and after completion of the test. The amount of moisture absorbed by a specimen is an important consideration in designing laminates for automotive components. Mositure adsorption is one factor in the failure of reinforced plastic laminates.

What is claimed is:

1. An apparatus for applying a variable bending load to a fiber reinforced plastic test specimen, said apparatus comprising:
    an elongated rectangular metal frame member, said frame member having an arcuate shape with the ends of said frame member being shaped to retain said test specimen;
    means secured to the center of the frame for applying a bending load, said means comprising a threaded member that engages a threaded opening dispersed in said frame; and
    a pair of elongated tubular members, one of said tubular members being attached to each end of said frame member with the axis of the tubular member at substantially a right angle to the axis of the frame member.

2. The apparatus of claim 1 wherein the test specimen is retained in the frame member by the ends of the frame member that are bent inwardly towards the cent of the frame member.

3. A method for testing fiber reinforced plastic laminates comprising:
   preparing an elongated test specimen of said laminate;
   placing said test specimen in a metal frame member under a bending load;
   weighing the test specimen and frame member to obtain an initial weight;
   subjecting the test specimen and frame member to desired temperature and humidity conditions for a preset time while said test specimen is under said bending load; and
   weighing the test specimen and frame member after they are subjected to the desired temperature and humidity conditions to obtain a final weight, the difference in the initial and final weights being the moisture absorbed by the test specimen.

* * * * *